United States Patent
Murpani et al.

(10) Patent No.: US 9,895,325 B2
(45) Date of Patent: *Feb. 20, 2018

(54) TABLET COMPOSITION COMPRISING CINACALCET HYDROCHLORIDE

(71) Applicant: SYNTHON B.V., CM Nijmegen (NL)

(72) Inventors: Deepak Murpani, CM Nijmegen (NL); Marta Vivancos Martinez, Sant Boi de Llobregat (ES)

(73) Assignee: Synthon B.V., Nijmegen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 14/654,317

(22) PCT Filed: Dec. 19, 2013

(86) PCT No.: PCT/EP2013/077523
§ 371 (c)(1),
(2) Date: Jun. 19, 2015

(87) PCT Pub. No.: WO2014/096277
PCT Pub. Date: Jun. 26, 2014

(65) Prior Publication Data
US 2015/0328172 A1    Nov. 19, 2015

(30) Foreign Application Priority Data
Dec. 21, 2012    (WO) .................. PCT/EP2012/076732

(51) Int. Cl.
*A61K 31/137*    (2006.01)
*A61K 9/20*    (2006.01)

(52) U.S. Cl.
CPC .......... *A61K 31/137* (2013.01); *A61K 9/2027* (2013.01); *A61K 9/2054* (2013.01); *A61K 9/2059* (2013.01); *A61K 9/2077* (2013.01)

(58) Field of Classification Search
CPC ... C07C 211/30; C07C 209/16; C07C 29/147; C07C 51/36; C07C 33/483; C07C 57/58; C07C 59/50
See application file for complete search history.

(56) References Cited

U.S. PATENT DOCUMENTS
7,829,595 B2    11/2010    Lawrence et al.

FOREIGN PATENT DOCUMENTS

| EP | 1 203 761 A2 | 5/2002 | |
|----|----|----|----|
| WO | WO2005/034928 A1 * | 4/2005 | ............. A61K 31/00 |
| WO | WO 2005/034928 A1 | 4/2005 | |
| WO | WO2008/068625 A2 * | 6/2008 | ........... C07C 209/28 |
| WO | WO 2008/068625 A2 | 6/2008 | |
| WO | WO 2010/034497 A2 | 4/2010 | |
| WO | WO 2011/146583 A2 | 11/2011 | |
| WO | WO 2013/107503 A1 | 7/2013 | |

OTHER PUBLICATIONS

International Search Report and Written Opinion for International Application No. PCT/EP2013/077523, European Patent Office, Netherlands, dated Apr. 4, 2014.

* cited by examiner

*Primary Examiner* — Audrea Buckley
(74) *Attorney, Agent, or Firm* — Mark R. Buscher

(57) ABSTRACT

The present invention relates to a tablet composition comprising a therapeutically effective dose of cinacalcet hydrochloride having a particle size distribution $D_{90}$ equal to or less than 30 μm in an amount of from 40% to 60% by weight based on the total weight of the composition, and one or more pharmaceutically acceptable excipients.

18 Claims, 2 Drawing Sheets

TABLET COMPOSITION COMPRISING CINACALCET HYDROCHLORIDE

BACKGROUND OF THE PRESENT INVENTION

The present invention relates to a pharmaceutical composition, particularly a tablet composition comprising a high drug load of cinacalcet hydrochloride, having improved bioavailability.

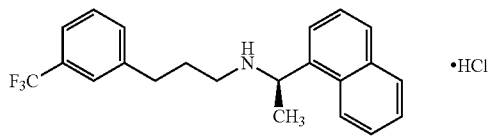 [SMILES: C[C@@H](NCCCc1cccc(C(F)(F)F)c1)c1cccc2ccccc12 ; Cl]

Cinacalcet, having the chemical structure shown above, is a calcimimetic agent, and as such it increases the sensitivity to extracellular calcium of the calcium-sensing receptors of the parathyroid gland, leading to reduced levels of parathyroid hormone, serum calcium, and phosphate. It is indicated for the treatment of secondary hyperparathyroidism in patients with chronic kidney disease on dialysis.

Cinacalcet free base and pharmaceutically acceptable salts thereof are disclosed in European Patent application EP1203761.

A cinacalcet hydrochloride-containing pharmaceutical product is approved in many countries of the world under the brand name Mimpara® (Amgen) in the EU and Sensipar® (Amgen) in the US. Generally, the marketed cinacalcet hydrochloride tablets comprise 30, 60 or 90 mg of cinacalcet hydrochloride.

Cinacalcet hydrochloride is poorly soluble in water and has a pH dependent solubility. At basic pH it is practically insoluble (<0.001 mg/ml). The solubility is about 1.6 mg/ml at a pH range of from about 3-5, however at pH 1 the solubility decreases to approx. 0.1 mg/ml. In the state of the art, various proposals have been made on how to formulate this active pharmaceutical ingredient.

The marketed formulation of cinacalcet hydrochloride is described in WO2005034928. The tablet composition disclosed therein contains cinacalcet hydrochloride with a particle size distribution $D_{50}$ less than or equal to 50 μm (see paragraph [021]) in an amount of approx. 18% by weight based on the total weight of the tablet composition (see paragraphs [019] and [057]).

The tablet of WO2005034928 contains a high amount (i.e. 70% by weight) of diluent among other pharmaceutical excipients, having a tablet weight of up to 540 mg for the cinacalcet 90 mg tablet strength. The incorporation of a relatively high amount of excipients (e.g., diluents and disintegrants) into the formulation of a solid oral dosage form can improve the dissolution rate of active pharmaceutical ingredients, especially those that are relatively hydrophobic and poorly soluble in water like cinacalcet. Increasing the amount of excipients in the composition, however, entails a number of disadvantages. Notably, tablet size will increase significantly causing patient compliance problems. In addition, content uniformity can be problematic as well as stability problems can occur related to interaction of the active pharmaceutical ingredient with one or more of the excipients.

The objective of the present invention was therefore to overcome the above-mentioned disadvantages.

DETAILED DESCRIPTION OF THE PRESENT INVENTION

Figure 1:
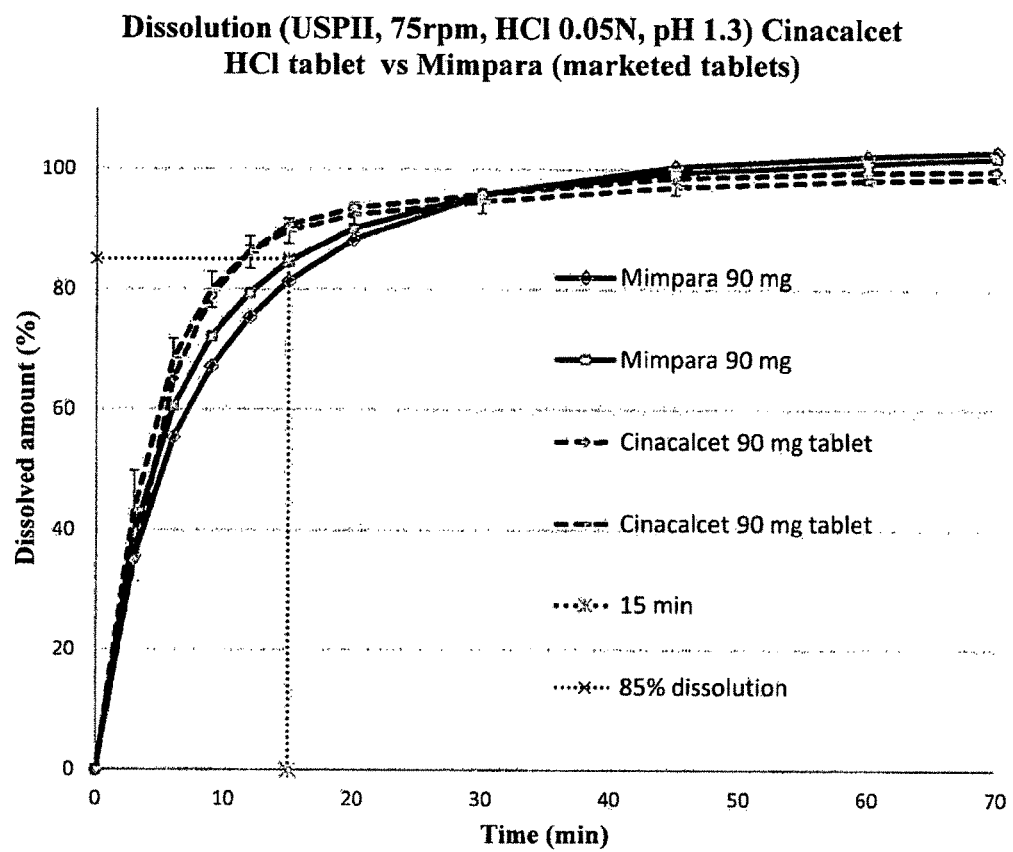
FIG. 1 shows the in vitro dissolution profiles of 90 mg cinacalcet hydrochloride tablets in accordance with the present invention as compared to commercially available Mimpara® 90 mg tablets.

The present invention relates to a pharmaceutical composition containing a high amount of cinacalcet hydrochloride having a particle size distribution $D_{90}$ equal to or less than 30 μm, preferably equal to or less than 25 μm, more preferably equal to or less than 10 μm, exhibiting good drug release and bioavailability profile. The preferred tablet composition has a high drug load, a reduced size and is bioequivalent as compared to the commercially available tablet.

In one embodiment, the present invention relates to a tablet composition comprising a therapeutically effective dose of cinacalcet hydrochloride having a particle size distribution $D_{90}$ equal to or less than 30 μm, preferably equal to or less than 25 μm, more preferably equal to or less than 10 μm, in an amount of from 40% to 60%, preferably from 45% to 55% by weight based on the total weight of the composition, and one or more pharmaceutically acceptable excipients.

The $D_{90}$ value of the particle size distribution is defined as the particle diameter at which 90% by volume of the particles have a smaller diameter than the diameter which corresponds to the $D_{90}$ value measured by laser diffractometry. Specifically, a Malvern Instruments Mastersizer was used to determine the particle size distribution.

The one or more pharmaceutically acceptable excipients to be used in accordance with the present invention can be chosen from, for example, diluents, binders, disintegrants, lubricants, and glidants.

Diluents are fillers which are used to increase the bulk volume of a tablet or capsule. Generally, by combining a diluent with the active pharmaceutical ingredient, the final product is given adequate weight and size to assist in production and handling. Binders hold the excipients that are present in a tablet together. Binders ensure that tablets and granules can be formed having the desired or required mechanical strength, and they give volume to low active dose tablets. Suitable examples of diluents to be used in accordance with the present invention include starch, pregelatinized starch, microcrystalline cellulose, and calcium phosphate, lactose, sorbitol, mannitol and sucrose.

The tablet composition of the present invention preferably contains at least one hydrophilic diluents. Starch, pregelatinized starch, lactose, sorbitol, mannitol and sucrose are suitable hydrophilic diluents.

In a preferred embodiment of the present invention, the at least one hydrophilic diluent is pregelatinized starch.

The tablet composition of the invention preferably comprises:
a) from 30% to 50% of one or more diluents by weight based on the total weight of the composition;
b) at least one binder in an amount of from 1% to 5% by weight based on the total weight of the composition.

Binders which are suitable for use in accordance with the present invention include povidone, hydroxypropyl methylcellulose, dihydroxy propylcellulose, and sodium carboxyl methylcellulose. Binders are preferably used in an amount of from 1% to 5% by weight based on the total weight of the composition. A preferred binder is povidone.

The tablet composition of the present invention may also contain a disintegrant. Disintegrants are added to a tablet composition to promote the breakup of the tablet into smaller fragments in an aqueous environment, thereby increasing the available surface area and promoting a more rapid release of the active pharmaceutical ingredient. Suitable examples of disintegrants to be used in accordance with the present invention include crospovidone, sodium starch glycolate, croscarmellose sodium, and mixtures of any of the foregoing. Disintegrants preferably are used in an amount of from 1% to 10% by weight based on the total weight of the composition.

The tablet composition of the invention may also contain a lubricant. Lubricants are generally used in order to reduce sliding friction. In particular, to decrease friction at the interface between a tablet's surface and the die wall during ejection, and reduce wear on punches and dies. Suitable lubricants to be used in accordance with the present invention include magnesium stearate, calcium stearate, stearic acid, glyceryl behenate, hydrogenated vegetable oil, and glycerine fumarate. The tablet composition of the invention may also contain a glidant. Glidants enhance product flow by reducing interparticulate friction. A suitable example is colloidal silicon dioxide.

Lubricants and glidants preferably are used in a total amount of from 0.05% to 5% by weight based on the total weight of the composition.

In a preferred embodiment, the tablet composition of the present invention contains the following ingredients, based on the total weight of the composition:

a. A therapeutically effective dose of cinacalcet hydrochloride in an amount of from 45% to 55% by weight;
b. Microcrystalline cellulose or pregelatinized starch or a mixture thereof in an amount of from 30% to 50% by weight;
c. Povidone in an amount of from 1% to 5% by weight;
d. Crospovidone in an amount of from 1% to 10% by weight; and
e. From 0.05% to 5% by weight of a lubricant and a glidant.

In one embodiment of the present invention, the therapeutically effective dose of cinacalcet hydrochloride is 30 mg, 60 mg or 90 mg.

The pharmaceutically acceptable excipients to be used in accordance with the present invention, can be used only intragranularly, only extragranularly, or both.

The present invention further relates to a tablet composition as described hereinabove, prepared by a wet-granulation process, which process comprises:

1. Mixing cinacalcet hydrochloride and one or more pharmaceutically acceptable excipients to form a mixture;
2. Wet-granulating the resulting mixture;
3. Further mixing the obtained granulate with one or more further pharmaceutically acceptable excipients to form a further mixture;
4. Compressing the mixture obtained in step (3) into a tablet; and optionally
5. Coating the tablet.

The present invention still further relates to a granulate suitable for making a tablet composition as described hereinabove, prepared by a wet-granulation process, which process comprises:

1. Mixing cinacalcet hydrochloride and one or more pharmaceutically acceptable excipients to form a mixture, and
2. Wet-granulating the resulting mixture.

In a preferred embodiment, the granulate of the invention contains an hydrophilic diluent. More preferably it contains pregelatinized starch and optionally other hydrophilic diluents. Pregelatinized starch is an excipient that generally can act as a diluent but also as binder improving cohesion of the granulate. We have found that surprisingly by adding pregelatinized starch intragranularly to our formulation, the dissolution profile is improved. This improvement is significant when compared to other known diluents and binders. Pregelatinized starch creates a hydrophilic environment that facilitates tablet disintegration and improves the dissolution of Cinacalcet significantly more than any other similar hydrophilic diluents.

The granules of the present invention typically have a particle size distribution $D_{50}$ of from 200-300 μm.

The present invention also relates to a pharmaceutical composition comprising a granulate as described hereinabove in the form of a capsule or a tablet, preferably a tablet.

The pharmaceutical compositions described herein can be made using conventional methods and equipment well-known in the art.

The pharmaceutical (tablet) compositions of the present invention have a high load of cinacalcet hydrochoride and show an in vitro dissolution profile wherein at least 75% of cinacalcet is released at thirty minutes when the composition is subjected to a dissolution study in 900 ml HCl 0.05N (pH 1.3) using a USP apparatus II at 75 rpm at 37° C. Preferably, at least 85% of cinacalcet is released from the pharmaceutical composition at thirty minutes and the tablet compositions in accordance with the present invention are bioequivalent in vitro and in vivo to the commercially available cinacalcet hydrochloride tablets.

FIG. 1 shows the in vitro dissolution profile of tablet compositions in accordance with the present invention as compared to commercially available tablets.

The present invention is illustrated by the following Examples.

EXAMPLES

Example 1

Three strengths of cinacalcet hydrochloride tablets were prepared in a conventional way as described further herein below, and have the following compositions:

| | % (w/w) | 30 mg | 60 mg | 90 mg |
|---|---|---|---|---|
| Intragranular | | | | |
| Cinacalcet hydrochloride | 50.860 | 33.06 | 66.12 | 99.18 |
| Pregelatinized starch (Starch 1500) | 33.378 | 21.70 | 43.39 | 65.09 |
| Crospovidone (Polyplasdone XL-10) | 2.000 | 1.30 | 2.60 | 3.90 |
| Povidone (Plasdone K29/32) | 2.000 | 1.30 | 2.60 | 3.90 |
| Purified water | qs | qs | qs | qs |
| Extragranular | | | | |

-continued

|  | % (w/w) | 30 mg | 60 mg | 90 mg |
|---|---|---|---|---|
| Microcrystalline cellulose (Avicel PH102) | 7.262 | 4.72 | 9.44 | 14.16 |
| Crospovidone (Polyplasdone XL) | 3.000 | 1.95 | 3.90 | 5.85 |
| Colloidal silicon dioxide (Colloidal anhydrous silica) | 0.500 | 0.33 | 0.65 | 0.98 |
| Magnesium stearate | 1.000 | 0.65 | 1.30 | 1.95 |
| Core tablet | 100.000 | 65.00 | 130.00 | 195.00 |
| Opadry II 85F210073 | 4.000 | 2.60 | 3.35 | 7.80 |
| Coated tablet | 104.000 | 67.60 | 133.35 | 202.80 |

Example 2

Cinacalcet hydrochloride 90 mg tablets

|  | % (w/w) | 90 mg |
|---|---|---|
| Intragranular | | |
| Cinacalcet hydrochloride | 50.09 | 99.18 |
| Pregelatinized starch (Starch 1500) | 32.87 | 65.09 |
| Crospovidone (Polyplasdone XL-10) | 2.95 | 5.8 |
| Povidone (Plasdone K29/32) | 1.97 | 3.90 |
| Purified water | qs | qs |
| Extragranular | | |
| Microcrystalline cellulose (Avicel PH102) | 7.68 | 15.21 |
| Crospovidone (Polyplasdone XL) | 2.96 | 5.85 |
| Colloidal silicon dioxide (Colloidal anhydrous silica) | 0.49 | 0.98 |
| Magnesium stearate | 0.98 | 1.95 |
| Core tablet | 100.000 | 198.00 |
| Opadry II, green | 4.000 | 7.92 |
| Coated tablet |  | 205.92 |

Figure 2:
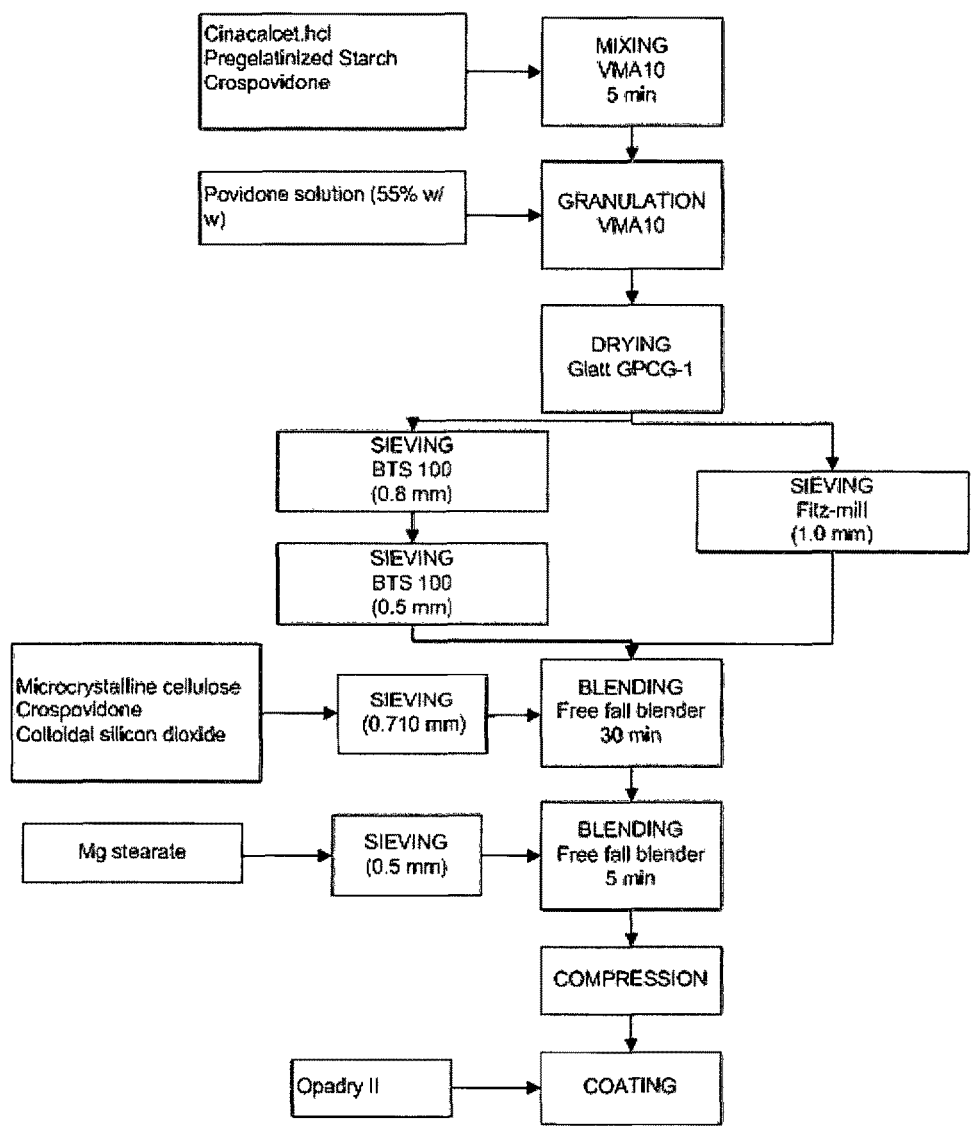
FIG. 2 depicts the process used to make the tablets of Examples 1 and 2.

The 30, 60 and 90 mg tablets of Example 1 and 2 were made according to the process depicted in FIG. 2.

FIG. 1 shows the in vitro dissolution profiles of 90 mg cinacalcet hydrochloride tablets in accordance with the present invention as compared to commercially available Mimpara® 90 mg tablets.

The invention claimed is:

1. A high drug load tablet composition comprising:
   a) a therapeutically effective dose of cinacalcet hydrochloride in an amount from 45% to 55% by weight;
   b) from 30% to 50% of pregelatinized starch by weight based on the total weight of the composition;
   c) at least one binder in an amount of from 1% to 5% by weight based on the total weight of the composition;
   d) a disintegrant in an amount of from 1% to 10% by weight based on the total weight of the composition;
   e) a lubricant and a glidant in a total amount of from 0.05% to 5% by weight based on the total weight of the composition, and
   wherein the cinacalcet hydrochloride has a $D_{90}$ equal to or less than 30 μm.

2. The high drug load tablet composition according to claim 1, wherein the cinacalcet hydrochloride has a $D_{90}$ equal to or less than 25 μm.

3. The high drug load tablet composition according to claim 2, wherein the cinacalcet hydrochloride has a $D_{90}$ equal to or less than 10 μm.

4. The high drug load tablet composition according to claim 1, wherein the therapeutically effective dose of cinacalcet hydrochloride is 90 mg.

5. The high drug load tablet composition according to claim 1, wherein the therapeutically effective dose of cinacalcet hydrochloride is 60 mg.

6. The high drug load tablet composition according to claim 1, wherein the therapeutically effective dose of cinacalcet hydrochloride is 30 mg.

7. The high drug load tablet composition according to claim 1, wherein the binder is selected from the group consisting of povidone, hydroxypropyl methylcellulose, dihydroxy propylcellulose, and sodium carboxyl methylcellulose.

8. The high drug load tablet composition according to claim 1, wherein the lubricant is selected from the group consisting of magnesium stearate, calcium stearate, stearic acid, glyceryl behenate, hydrogenated vegetable oil, and glycerine fumarate.

9. A high drug load tablet composition comprising a therapeutically effective amount of cinacalcet hydrochloride prepared by a wet-granulation process comprising:
   a) mixing cinacalcet hydrochloride, pregelatinized starch, and one or more pharmaceutically acceptable excipients to form a mixture;
   b) wet-granulating the resulting mixture;
   c) further mixing the obtained granulate with one or more further pharmaceutically acceptable excipients to form a further mixture;
   d) compressing the mixture obtained in step (c) into a tablet; and optionally
   e) coating the tablet, and
   wherein said cinacalcet hydrochloride comprises 45%-55% by weight of said tablet and said pregelatinized starch comprises 30%-50% by weight of said tablet.

10. The high drug load tablet composition according to claim 9, wherein the one or more further pharmaceutically acceptable excipients of step (c) comprises povidone.

11. The high drug load tablet composition according to claim 10, wherein at least 85% of cinacalcet hydrochloride is released at thirty minutes when the composition is subjected to a dissolution study in 900 ml HCl 0.05N (pH 1.3) using USP apparatus II at 75 rpm at 37° C.

12. The high drug load tablet composition according to claim 1, wherein the composition comprises:
   a) 30 mg of cinacalcet hydrochloride,
   b) 21.70 mg of pregelatinized starch,
   c) 1.30 mg of crospovidone,
   d) 1.30 mg of povidone,
   e) 0.33 mg of colloidal silicon dioxide, and
   f) 0.65 mg of magnesium stearate.

13. The high drug load tablet composition according to claim 1, wherein the composition comprises:
   a) 60 mg of cinacalcet hydrochloride,
   b) 43.39 mg of pregelatinized starch,
   c) 2.60 mg of crospovidone,
   d) 2.60 mg of povidone,
   e) 0.65 mg of colloidal silicon dioxide, and
   f) 1.30 mg of magnesium stearate.

14. The high drug load tablet composition according to claim 1, wherein the composition comprises:
   a) 90 mg of cinacalcet hydrochloride,
   b) 65.09 mg of pregelatinized starch,
   c) 3.90 mg of crospovidone,
   d) 3.90 mg of povidone,
   e) 0.98 mg of colloidal silicon dioxide, and
   f) 1.95 mg of magnesium stearate.

15. The high drug load tablet composition according to claim 1, wherein the composition comprises:

a) about 50% (w/w) of cinacalcet hydrochloride,
b) 33% (w/w) of pregelatinized starch,
c) 2% (w/w) of crospovidone,
d) 2% (w/w) of povidone,
e) 0.5% (w/w) of colloidal silicon dioxide, and
f) 1% (w/w) of magnesium stearate.

16. The high drug load tablet composition according to claim 1, wherein at least 85% of cinacalcet hydrochloride is released at thirty minutes when the composition is subjected to a dissolution study in 900 ml HCl 0.05N (pH 1.3) using USP apparatus II at 75 rpm at 37° C.

17. A pharmaceutical tablet composition comprising:
a) a therapeutically effective dose of cinacalcet hydrochloride in an amount from 45% to 55% by weight;
b) pregelatinized starch in an amount of 30% to 50% by weight;
c) povidone in an amount of from 1% to 5% by weight;
d) crospovidone in an amount of from 1% to 10% by weight; and
e) a lubricant and a glidant in a total amount of from 0.05% to 5% by weight;
wherein the cinacalcet hydrochloride has a $D_{90}$ equal to or less than 30 μm and wherein at least 85% of cinacalcet hydrochloride is released at thirty minutes when the tablet is subjected to a dissolution study in 900 ml HCl 0.05N (pH 1.3) using USP apparatus II at 75 rpm at 37° C.

18. The tablet according to claim 17, wherein said therapeutically effective dose of cinacalcet hydrochloride is selected from 30 mg, 60 mg, and 90 mg.

* * * * *